United States Patent [19]
Idoff et al.

[11] Patent Number: 5,077,836
[45] Date of Patent: Jan. 7, 1992

[54] HEADGEAR

[75] Inventors: Dag Idoff, Apelvägen; Södra Tvärgatan, Malin Österström, both of Sweden

[73] Assignee: Bilsom AB, Billesholm, Sweden

[21] Appl. No.: 469,606

[22] PCT Filed: Oct. 13, 1988

[86] PCT No.: PCT/SE88/00535
§ 371 Date: May 16, 1990
§ 102(e) Date: May 16, 1990

[87] PCT Pub. No.: WO89/04124
PCT Pub. Date: May 18, 1989

[30] Foreign Application Priority Data
Nov. 2, 1987 [SE] Sweden .................................. 8704271

[51] Int. Cl.⁵ .................................................. A61F 9/00
[52] U.S. Cl. ............................................... 2/10; 2/8; 2/417
[58] Field of Search ................... 2/7, 8, 10, 171, 183, 2/417, 418, 419

[56] References Cited

U.S. PATENT DOCUMENTS

| | | | |
|---|---|---|---|
| 2,187,932 | 1/1940 | Cornell | 2/8 |
| 2,437,748 | 3/1948 | Malcom | 2/419 |
| 3,075,201 | 1/1963 | Lindblom | 2/8 |
| 3,866,244 | 2/1975 | Ruck | 2/419 |
| 4,464,800 | 8/1984 | Edwards | 2/8 |
| 4,649,571 | 3/1987 | Falkiner | 2/8 |

FOREIGN PATENT DOCUMENTS

| | | | |
|---|---|---|---|
| 2220977 | 10/1974 | France | 2/8 |
| 594079 | 11/1947 | United Kingdom | 2/8 |

Primary Examiner—Werner H. Schroeder
Assistant Examiner—Michael A. Neas

[57] ABSTRACT

Headgear for mounting protective equipment such as a visor is disclosed as including a head band and a crown band. The head band includes a brow band section, side band sections and a neck band section. The side band sections are curved upwardly and incline inwardly such that the neck band section is positioned lower than the brow band section when the headgear is worn. The sections of the side bands that are inclined are reinforced at a top edge of the side band portions.

20 Claims, 3 Drawing Sheets

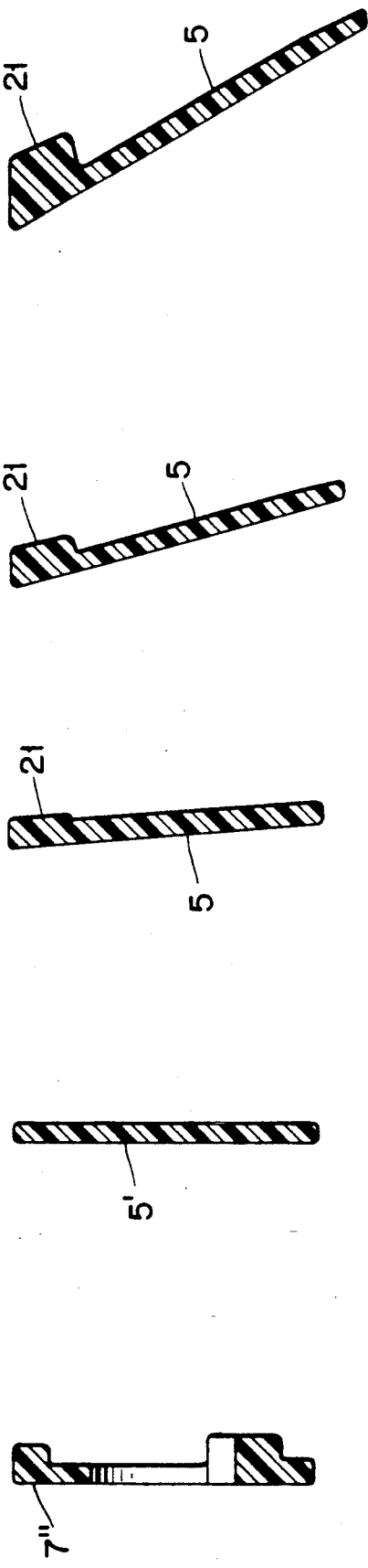
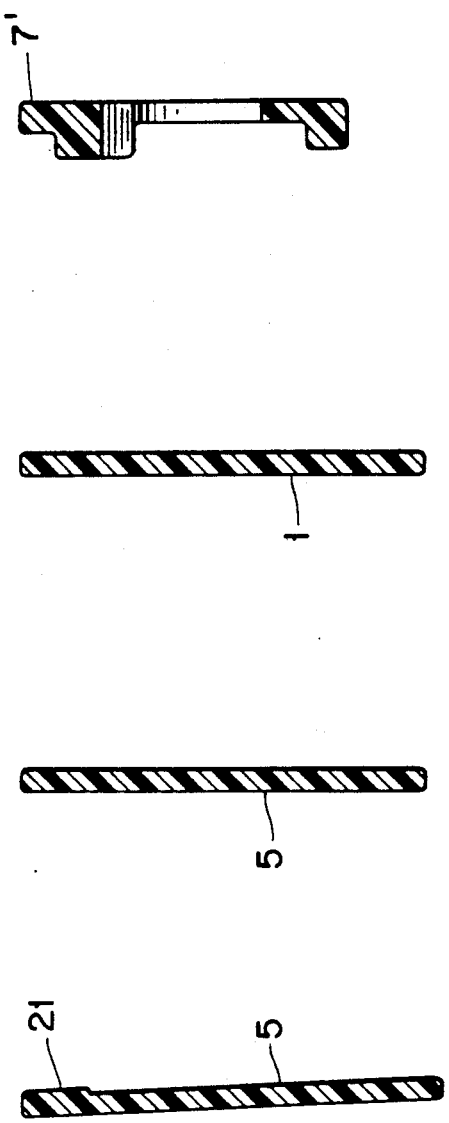
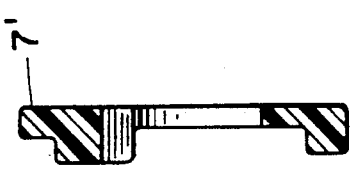
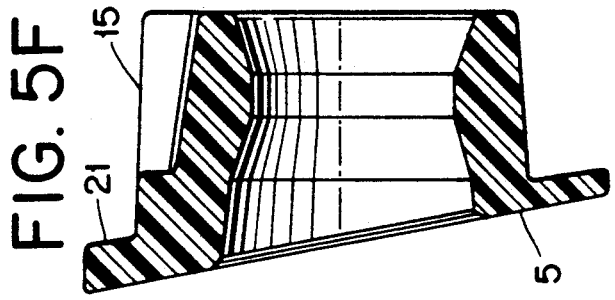

HEADGEAR

TECHNICAL FIELD

The present invention relates to a headgear to be worn on the head of a person, for the mounting of protective equipment, e.g. a visor, said headgear comprising a head band encircling the head of the person and including a brow band portion, two side band portions and a neck band portion, and a crown support means, such as a crown band adjustable in length and connected to the head band and offering support against the crown when the headgear is being worn.

TECHNICAL BACKGROUND

Conventional headgears of the type described in the introduction have a head band the band plane of which is located substantially vertically around the loop formed by the head band. This loop lies in substantially a single plane. The head band has a homogeneous thickness. The neck band portion is usually provided with means enabling adjustment of the circumferential length of the head band, i.e. adjustment to different head sizes.

Although headgears of this type often function satisfactorily, some people may find them uncomfortable to wear in view of an inadequate adjustability to the shape of the head. Furthermore, headgears of this type are often easily dislodged if the person wearing the headgear moves the head carelessly particularly if he inclines the head considerably. In order to solve this latter problem it has been suggested to provide the headgear with extra retaining bands secured to the head band and cooperating with lower portions of the nape of the neck. However, a solution of this kind is not good with regard to the possibilities of simple adjustment and fitting of the headgear.

Another problem with the known headgears is the fact that they unfavourably affect the wearer's possibilities to use spectacles, earmuffs, etc. since there is disturbing interference in the region of each ear.

OBJECT OF THE INVENTION

The object of the present invention is to provide an improved headgear of the type described in the introduction, whereby the drawbacks and problems discussed above are alleviated to a great extent.

SUMMARY OF THE INVENTION

This object is achieved according to the invention by means of a headgear having the features defined in the accompanying claims.

The headgear according to the invention is thus substantially characterized in that the side band portions of the head band curve strongly upwards and incline inwardly over at least a substantial portion of their curved section. At the back, the side band portions extend downwardly so that the neck band portion will be located considerably lower than the brow band portion when the headgear is worn. Furthermore, the side band portions are preferably reinforced at their upper edge, at least over a portion of their inwardly inclined section.

The side band portions preferably curve upwardly directly from the connection point with the brow band portion. The latter is also preferably curved to a certain extent at the ends, thus giving a gently curved rounded transistion between the brow band portion and the side band portions.

The upwardly curved, inwardly inclined side band portions have been found to result in the headgear fitting well and uniformly around the entire head and offering an extremely good fit irrespective of the size and shape of the head. The curved shape also means that the side band portions are "cut high" above the ears, thus leaving the ears free for cooperation with the side pieces of a pair of glasses, earmuffs, etc. This also allows earmuffs, for instance, to be carried by the headgear.

The headgear is suitably provided with a tensioning mechanism in the neck portion, enabling adjustment of the length of the head band. It has been found that the curved, inwardly inclined side band portions offer still better fit to the head, thereby increasing comfort, when adjusting the length of the head band with the tensioning mechanism, if the side band portions are reinforced at their upper edge. Advantageously, such reinforcement can be achieved by making the side band portions thicker at their upper edge, i.e. by means of an external rib, bead or the like. It is also feasible for the side band portions to increase in thickness more or less continuously from the lower to the upper edge.

The upward curve of the side band portions allows the brow band to be placed low down on the brow. Together with the neck band portion, located even lower, this means that the headgear according to the invention stays very firmly on the wearer's head.

The invention will be described more fully in the following with reference to an embodiment shown by way of example, with reference to the accompanying drawings.

BRIEF DESCRIPTION OF THE DRAWINGS

FIGS. 5a-5j show different sections through the blank according to FIG. 3.

DESCRIPTION OF EMBODIMENT

Figure 1:
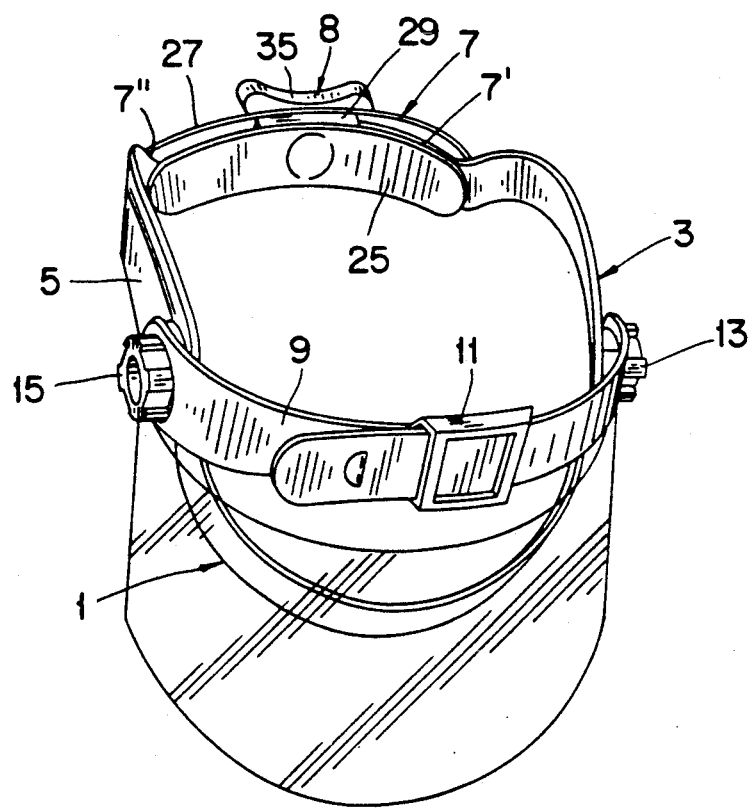
FIG. 1 is a schematically perspective view of a headgear in accordance with the invention, seen at an angle from above.

The headgear shown in the drawings comprises a head band and a crown band. The head band comprises a brow band portion 1, two side band portions 3, 5 and a neck band portion 7. The head band is made in one piece of an injection moulded band element (see FIGS. 3 and 4) with the exception of the conventional tensioning mechanism 8 in the neck band portion 7. The parts of the injection moulded band element forming the neck band portion are designated 7' and 7" (see FIG. 3 in particular).

The crown support 9 is of conventional design and includes a tensioning means 11 in the form of a slide fastener. The two ends of the crown band 9 are pivotally connected, also in a conventional manner, to attachments 13, 15 on the front parts of the side band portions. The attachments 13, 15 are also designed for the attachment of protection means such as a visor, to be carried on the headgear. The attachments are conventional and need not therefore be further described here.

Figure 3:
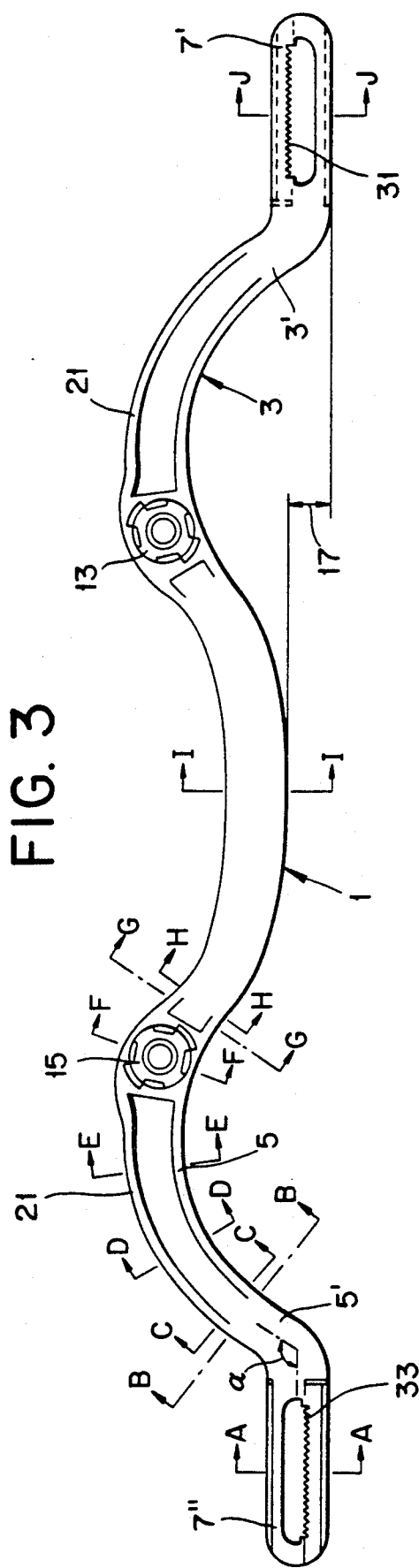
FIG. 3 is a side view of a head-band blank.
Figure 4:
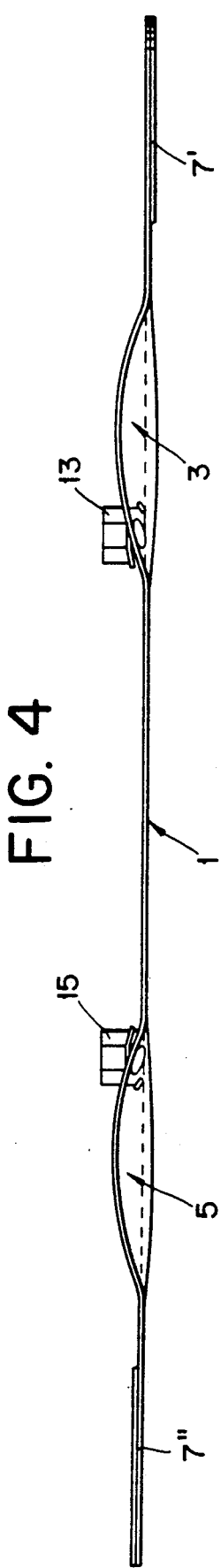
FIG. 4 is a view from below of the blank according to FIG. 3.

The brow band portion 1 is located substantially in a vetical plane (relative to the normal position of use on a person with his head upright) although inclined slightly backwards and with its two ends bent somewhat back from this plane at the rounded transition to the side band portions 3, 5. The ends are also somewhat upwardly curved, thus producing a certain concave arc form as shown in FIG. 3. This ensures a good fit to the special shape of the side band portions.

Figure 2:
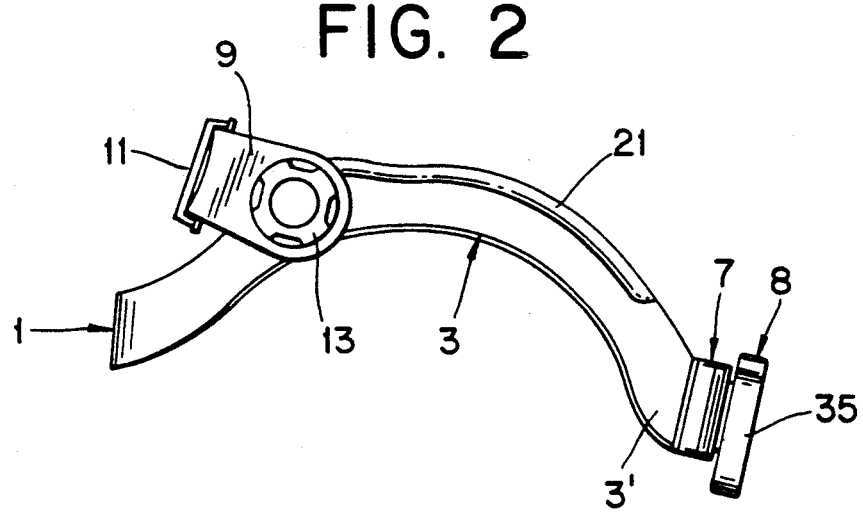
FIG. 2 is a schematic side view of the headgear according to FIG. 1.

As is clear in FIGS. 2 and 3, in particular, the side band portions 3, 5 curve upwardly in a convex arc which can be roughly considered as part of a circle arc (with a typical radius of the order of 10 cm). The rear, downwardly extending ends 3', 5' of the side band portions are extended so that the connecting neck band parts 7', 7" will lie at a considerably lower level than the brow band portion 1. This level difference is intimated in FIG. 3 at 17.

The curved side band portions 3, 5 incline inwardly along most of their length, i.e. the upper edges are closer together than the corresponding lower edges. This inclination is clearest in FIGS. 4 and 5. The inclination is greatest at the mid-portion of the band portions and decreases in both directions, substantially disappearing before the transitions to the brow and neck band portions, respectively. Maximum inclination in relation to the vertical plane may be typically between 20° and 30°.

The head band is made of a plastic material having a suitable combination of shape permanence and flexibility. In view of the special design of the side band portions and the fact that using the tensioning means to tighten the neck band portion entails a certain influence on the side band portions, it has been found advantageous for the inwardly inclined portions of the side bands to be reinforced at the upper edge. The upper edge has therefore been provided with an external rib or bead 21, the thickness of which increases with the inward inclination.

The neck band parts 7', 7" are substantially vertical, with horizontal extension, and substantially parallel to the brow band portion 1. The parts 7', 7" define a marked angle α to the direction of the ends of the side band portions 3, 5 (FIG. 3). The parts 7', 7" are also folded in towards each other, transversely to the side band portions, so that they are close together and can be mutually displaced longitudinally in the tensioning mechanism 8.

The tensioning mechanism 8 is of conventional design and consists of an inner, flexible neck-supporting band part 25, an outer support part 27 and an intermediate part 29 provided with a pinion (not shown) and through which the parts 7' and 7" pass. The pinion engages with corresponding upper and lower racks 31 and 33 on the parts 7' and 7" (see FIG. 3) and can be rotated by a knob 35. When the pinion is rotated, the parts 7' and 7" are moved in opposite directions. The knob 35 can thus be used to adjust the mutual position between the parts 7' and 7", thus adjusting the fit of the headgear to the wearer's head. The parts 7' and 7" are screwed as far apart as possible in the position shown in FIG. 1.

We claim:

1. Headgear to be worn on the head of a person, for the mounting of protective equipment comprising a head band encircling the head of the person, said head band including a brow band portion, a pair of side band portions, a neck band portion, and a crown support means, said crown support means including a crown band adjustable in length connected to said head band, said side band portions connecting said brow band portion to said neck band portion, each of said side band portions having a curved section that curves upwardly from said neck band portion towards said brow band portion such that said neck band portion is positioned substantially lower than said brow band portion when said headgear is positioned on the head of a user, each of said side band portions having a molded-in inclination towards each other over at least a substantial portion of said curved section such that top edges of said side band portions are closer in proximity to each other than bottom edges of said side band portions.

2. Headgear as claimed in claim 1, wherein said top edges of said side band portions include a reinforced portion over a substantial portion of said curved section.

3. Headgear as claimed in claim 1, wherein each end of said brow band portion is upwardly curved so as to form a smooth transition between said brow band portion and said curved section of each of said side band portions.

4. Headgear as claimed in claim 1, wherein said neck band portion includes a band part for each side portion that is connected to said neck band portion, each band part extending from a neck band end of a corresponding side band portion, each of said band parts extending at a predetermined angle to the curved section of the side band portions, said band parts being disposed inwardly towards each other, and said band parts being connected to each other by means for adjusting the size of said headgear.

5. Headgear as claimed in claim 1, wherein said head band is made of an injection moulded material.

6. Headgear as claimed in claim 1, wherein said head band further includes a length-adjusting tensioning mechanism, said mechanism being disposed in said neck band portion.

7. Headgear as claimed in claim 2, wherein said top edges of said side band portions are thicker in cross-section than said bottom edges to form said reinforced portion.

8. Headgear as claimed in claim 2, wherein each end of said brow band portion is upwardly curved so as to form a smooth transition between said brow band portion and said curved section of each of said side band portions.

9. Headgear as claimed in claim 2, wherein said neck band portion includes a band part for each side portion that is connected to said neck band portion, each band part extending from a neck band end of a corresponding side band portion, each of said band parts extending at a predetermined angle to the curved section of the side band portions, said band parts being disposed inwardly towards each other, and said band parts being connected to each other by means for adjusting the size of said headgear.

10. Headgear as claimed in claim 2, wherein said head band is made of an injection moulded material.

11. Headgear as claimed in claim 2, wherein said head band further includes a length-adjusting tensioning mechanism, said mechanism being disposed in said neck band portion.

12. Headgear as claimed in claim 7, wherein said top edges include one of an external rib and bead such that said top edges of said side band portion are thicker in cross-section than said bottom edges.

13. Headgear as claimed in claim 7, wherein each end of said brow band portion is upwardly curved so as to form a smooth transition between said brow band portion and said curved section of each of said side band portions.

14. Headgear as claimed in claim 7, wherein said neck band portion includes a band part for each side portion that is connected to said neck band portion, each band part extending from a neck band end of a corresponding side band portion, each of said band parts extending at a predetermined angle to the curved section of the side band portions, said band parts being disposed inwardly towards each other, and said band parts being connected to each other by means for adjusting the size of said headgear:

15. Headgear as claimed in claim 7, wherein said head band is made of an injection moulded material.

16. Headgear as claimed in claim 7, wherein said head band further includes a length-adjusting tensioning mechanism, said mechanism being disposed in said neck band portion.

17. Headgear as claimed in claim 12, wherein each end of said brow band portion is upwardly curved so as to form a smooth transition between said brow band portion and said curved section of each of said side band portions.

18. Headgear as claimed in claim 12, wherein said neck band portion includes a band part for each side portion that is connected to said neck band portion, each band part extending from a neck band end of a corresponding side band portion, each of said band parts extending at a predetermined angle to the curved section of the side band portions, said band parts being disposed inwardly towards each other, and said band parts being connected to each other by means for adjusting the size of said headgear.

19. Headgear as claimed in claim 12, wherein said head band is made of an injection moulded material.

20. Headgear as claimed in claim 12, wherein said head band further includes a length-adjusting tensioning mechanism, said mechanism being disposed in said neck band portion.

* * * * *